United States Patent [19]

Stephens, Sr.

[11] Patent Number: 5,103,677
[45] Date of Patent: Apr. 14, 1992

[54] METHOD AND APPARATUS FOR TESTING GAP FILLER MATERIALS

[75] Inventor: Gerald E. Stephens, Sr., Anaheim, Calif.

[73] Assignee: Northrop Corporation, Hawthorne, Calif.

[21] Appl. No.: 570,053

[22] Filed: Aug. 20, 1990

[51] Int. Cl.$^5$ .............................................. G01N 3/32
[52] U.S. Cl. ...................................... 73/812; 73/827; 324/701
[58] Field of Search ............... 324/693, 695, 699, 701; 73/808, 810, 811, 812, 813, 814, 815, 788, 818, 827, 842, 808

[56] References Cited

U.S. PATENT DOCUMENTS

| | | | |
|---|---|---|---|
| 3,192,474 | 6/1965 | Cherry | 324/693 |
| 3,803,485 | 4/1974 | Crites et al. | 324/693 |
| 4,974,451 | 12/1990 | DeTeresa | 324/701 |

Primary Examiner—Jerry W. Myracle
Attorney, Agent, or Firm—Terry J. Anderson; Robert B. Block; Karl J. Hoch, Jr.

[57] ABSTRACT

A system for testing the properties of a material used in sealing gaps between aircraft panels. The system includes a first device having a pair of interior plates positionable on opposite sides of a first specimen, a pair of intermediate plates located on the sides of the interior plates remote from the first specimen, a pair of exterior plates located on the sides of the intermediate plates remote from the specimen, drive shafts coupled to the exterior plates, a first mechanism connected to the drive shafts for imparting motion thereto, and a first electrical device connected to the interior plates for testing the properties of the first specimen during the operation of the first mechanism. The system also includes a second device having a pair of primary plates with interior portions spaced from each other, a pair of secondary plates secured to the interior portions of the primary plates on opposite sides of a second specimen, the second specimen being formed in a specimen-receiving space located entirely over only the interior portion of one of the primary plates, a second mechanism connected to the primary plates for imparting motion to at least one of the primary plates and its secured secondary plate, and a second electrical device connected to the secondary plates for testing the properties of the second specimen during the operation of the second mechanism. Also disclosed is a method of testing such specimen.

9 Claims, 5 Drawing Sheets

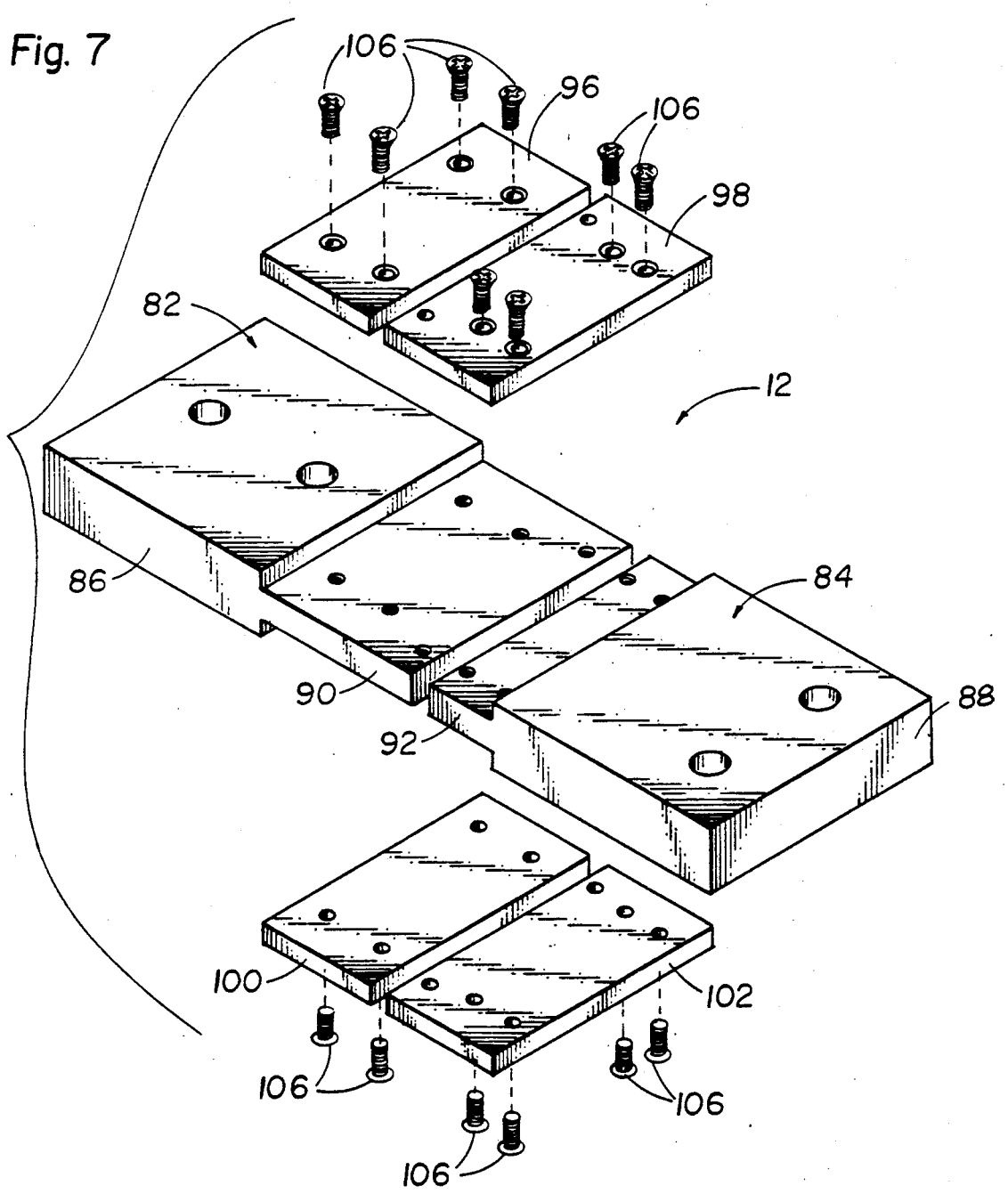

METHOD AND APPARATUS FOR TESTING GAP FILLER MATERIALS

BACKGROUND OF THE INVENTION

1. Summary of the Invention

This invention relates to a method and apparatus for testing gap filler materials and, more particularly, to a system for determining a plurality of mechanical and electrical properties of materials designed for use in filling spaces between aircraft plates.

2. Description of the Background Art

In the field of aircraft, metallic plates are coupled or otherwise secured together to lower base structures as by fasteners, set screws or other like mechanisms. Such other mechanisms are removable to allow for access to internal aircraft components and for the replacement and/or repair of the individual plates.

The proper engineering design of aircraft requires that adjacent plates be spaced a small distance from each other so as to allow for expansion and/or contraction of the plates during extreme thermal conditions. Such spacing also allows for plate shifting during the maneuvering of the aircraft during operation and use. Unfortunately, however, the spacing between plates creates a discontinuous surface which interrupts the laminar flow of air thereover. This results in undesirable drag, excessive sound, poor fuel consumption and diminished handling capabilities. In addition, the plates are normally electrically conductive thereby creating electrical discontinuities at the gaps which are detectable by radar. This is because the discontinuous electrical surfaces, as created by the spacings between plates, increases electrical interference when reflecting radar waves. This increases the detectability of the aircraft by radar.

From a commercial standpoint the most common technique for filling aircraft gaps is the use of an elastomeric filler material such as silicone, urethane or the like, foam or non-foamed, formed in place in the aircraft gap. Prior to forming, such filler material is loaded with an electrically conductive, electro-magnetic additive of a heavy metal such as nickel, silver, gold, ferraus metal or the like. Such filler material when properly loaded provides the desired electrical conductivity to abate electrical discontinuity. Unfortunately, however, determining the mechanical and electrical properties of such filler material, particularly while being subjected to varying mechanical and electrical conditions, is a difficult task.

The testing of mechanical and electrical properties of materials is the subject of a wide variety of commercial devices and patents. By way of example, note U.S. Pat. No. 4,095,461 to Starita. This patent measures shear properties of polymers while the present invention measures flatwise tensile strength, elongation, adhesion to substrates, fatigue capability and conductivity of conductive polymers, mechanical and electrical properties of the same time. U.S. Pat. No. 3,214,961 to Brown et al measures flatwise adhesion of sealant material between concrete members but not electrical properties, whereas the present invention tests conductive polymers and measures the flatwise tensile strength, elongation, fatigue capability and conductivity as well as the adhesion to a substrate. The same is true for U.S. Pat. No. 2,667,069 to Ramos et al. In addition, U.S. Pat. No. 4,089,211 to Vercellone et al; U.S. Pat. No. 2,595,069 to Fritz; U.S. Pat. No. 3,786,673 to Weissman and U.S. Pat. No. 3,621,711 to Griffith et al all relate to equipment for the testing of elastomeric materials, but none measures conductivity during flatwise tensile testing and fatigue cycles as in the present invention. Further, U.S. Pat. No. 3,572,102 to Baratta and U.S. Pat. No. 2,586,940 to Wolf are patents relating to electrical measurement. They have no relationship to the electrical measurements carried on during the flatwise tensile and fatigue testing as in the present invention. Lastly, U.S. Pat. No. 2,413,737 to Weaver relates to patch pull testing of aircraft skins and has no relationship to the flatwise tensile and fatigue testing of conductive polymers during electrical testing as in the present invention.

As illustrated by the large number of prior patents and commerical devices and techniques, efforts are continuously being expended in an effort to improve testing methods and apparatus for aircraft gap filler material and the like. Such efforts are being made to render the testing of such materials more efficient, reliable, inexpensive and convenient. None of these previous efforts, however, provides the benefits attendant with the present invention. Additionally, the prior patents and commercial devices and techniques do not suggest the present inventive combination of method steps and component elements arranged and configured as disclosed and claimed herein.

The present invention achieves its intended purposes objects and advantages through an unobvious combination of method steps and component elements, with the use of a minimum number of parts, at a reasonable cost to manufacture and use and by employing only readily available materials.

It is, therefore, an object of the present invention to provide an improved method and system for testing the mechanical and electrical properties of an electrically conductive specimen adapted for use in sealing gaps between aircraft panels, comprising a first device having a pair of electrically conductive interior plates positionable on opposite sides of a specimen, a pair of electrically insulating intermediate plates located on the sides of the interior plates remote from the specimen, a pair of electrically conductive exterior plates located on the sides of the intermediate plates remote from the specimen, means to couple to the exterior plates to drive means for imparting motion thereto with respect to the specimen, and means to couple the interior plates to electrical means for providing electrical current and for testing the electrical properties of the specimen during the operation of the drive means; and a second device having a pair of electrically insulating primary plates with interior portions spaced from each other, a pair of electrically conductive secondary plates secured to the interior portions of the primary plates so as to form a specimen-receiving space located entirely over only the interior portion of one of the primary plates, means to couple drive means with respect to the primary plates for imparting motion to at least one of the primary plates and its secured secondary plate with respect to the specimen, and attachment means to couple the secondary plates to electrical means for providing electrical current and for testing the electrical properties of the specimen during the operation of the drive means.

It is a further object of this invention to concurrently test aircraft gap filler material for mechanical and electrical properties.

It is a further object of the present invention to maximize specimen testing with minimum equipment.

It is a further object of this invention to manufacture superior aircraft.

The foregoing has outlined some of the more pertinent objects of the present invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown on the attached drawings. For the purpose of summarizing the invention, the invention may be incorporated into an improved system for testing the mechanical and electrical properties of an electrically conductive specimen adapted for use in sealing gaps between aircraft panels, comprising a first device having a pair of electrically conductive interior plates positionable on opposite sides of a specimen, a pair of electrically insulating intermediate plates located on the sides of the interior plates remote from the specimen, a pair of electrically conductive exterior plates located on the sides of the intermediate plates remote from the specimen, means to couple to the exterior plates to drive means for imparting motion thereto with respect to the specimen, and means to couple the interior plates to electrical means for providing electrical current and for testing the electrical properties of the specimen during the operation of the drive means; and a second device having a pair of electrically insulating primary plates with interior portions spaced from each other, a pair of electrically conductive secondary plates secured to the interior portions of the primary plates so as to form a specimen-receiving space located entirely over only the interior portion of one of the primary plates, means to couple drive means with respect to the primary plates for imparting motion to at least one of the primary plates and its secured secondary plate with respect to the specimen, and attachment means to couple the secondary plates to electrical means for providing electrical current and for testing the electrical properties of the specimen during the operation of the drive means.

The invention may also be incorporated into apparatus for testing the properties during the movement of an electrically conductive specimen adapted for use in sealing gaps between panels of aircraft, comprising a pair of spaced, electrically conductive, interior plates aligned and positionable on opposite sides of the specimen to be tested; a pair of spaced, electrically insulative, intermediate plates aligned with the interior plates and located on the sides of the interior plates remote from the specimen; a pair of spaced, electrically conductive, exterior plates aligned with the interior and intermediate plates and located on the sides of the intermediate plates remote from the specimen; a support fixture having corner block means and side walls coupled to an end wall for receiving and holding the exterior, intermediate and interior plates in proper position for receiving the specimen; bolts coupling the exterior, intermediate and interior plates for insuring concurrent movement of the plates on each side of the specimen; shafts coupled with respect to the exterior plates for coupling to a drive means to impart motion to the exterior, intermediate and interior plates with respect to the specimen; and attachment means to couple the interior plates to electrical means for the providing of electrical current and for the testing of the electrical properties of the specimen during the movement of the exterior, intermediate and interior plates.

The invention may also be incorporated into apparatus for testing the properties of an electrically conductive specimen adapted for use in sealing gaps between aircraft panels, comprising a pair of horizontally disposed primary plates of electrically insulating material axially aligned and laterally disposed with respect to each other, the primary plates having exterior portions of a thicker height and interior portions of a thinner height, the interior portions being of different lengths and spaced from each other to allow for relative longitudinal sliding movement of the primary plates with respect to each other; a pair of horizontally disposed secondary plates of electrically conductive material axially aligned and laterally disposed with respect to each other, the secondary plates being secured to the interior portions of the primary plates, the secondary plates being spaced from each other thereby forming a specimen-receiving space located entirely over only one of the interior portions of the primary plate for thereby allowing longitudinal sliding movement of the primary plates and their secured secondary plates with respect to each other; means to couple the primary plates to a drive means for imparting motion to the primary and secondary plates with respect to the specimen; and attachment means to couple the primary plates to electrical means for the providing of electrical current and for the testing of the electrical properties of the specimen during the movement of the primary and secondary plates with respect to the specimen.

The invention may also be incorporated into apparatus for testing a specimen, comprising a pair of spaced, electrically conductive, interior plates positionable on opposite sides of the specimen; a pair of spaced, electrically insulative, intermediate plates located on the sides of the interior plates remote from the specimen; a pair of spaced, electrically conductive, exterior plates located on the sides of the intermediate plates remote from the specimen; means to couple a drive means to the exterior plates for imparting motion to the plates with respect to the specimen; and means to couple the interior plates to electrical means for providing electrical current and for testing the electrical properties of the specimen during the movement of the plates.

The plates all have a plurality of holes extending therethrough and further included are bolts coupling the plates on opposite sides of the specimen for movement with respect to specimen. The apparatus further includes a support fixture having an end wall with corner blocks and side walls for receiving and holding the exterior, intermediate and interior plates in proper position for receiving the specimen.

The invention may also be incorporated into apparatus for testing a specimen comprising a pair of primary plates of electrically insulating material, the primary plates having exterior portions and interior portions, the interior portions being spaced from each other; a pair of secondary plates of electrically conductive material, the secondary plates being secured to the interior portions of the primary plates, the secondary plates being spaced from each other thereby forming a specimen-receiving space therebetween located entirely over only the interior portion of one of the primary plates for thereby allowing relative longitudinal sliding movement of the primary plates and their secured secondary plates with respect to each other and the specimen; means to couple drive means with respect to the primary plates for imparting motion to at least one of the primary plates and its secured secondary plates with respect to the specimen; and attachment means to couple the primary plates to electrical means for providing electrical current and for testing the electrical properties of the specimen during the movement of the drive means.

The apparatus further includes a second pair or supplemental plates located on the interior portions of the primary plates opposite from the first pair of secondary plates.

The invention may also be incorporated into a method for concurrently testing the mechanical and electrical properties of an electrically conductive specimen adapted for use in sealing gaps between aircraft panels, comprising the steps of providing a first device having a pair of electrically conductive interior plates positionable on opposite sides of a specimen, a pair of electrically insulative intermediate plates located on the sides of the interior plates remote from the specimen, and a pair of electrically conductive exterior plates located on the sides of the intermediate plates remote from the specimen; coupling the exterior plates to drive means; operating the drive means to impart motion to the exterior plates; and attaching the interior plates to electrical means for providing electrical current and for testing the electrical properties of the specimen during the operation of the drive means; and providing a second device having a pair of electrically insulating primary plates with interior portions spaced from each other, and a pair of electrically conductive secondary plates secured to the interior portions of the primary plates so as to form a specimen-receiving space located entirely over only the interior portion of one of the primary plates; coupling a drive means with the primary plates; operating the drive means to impart motion to at least one of the primary plates and its secured secondary plate; and attaching the secondary plates to electrical means for providing electrical current and for testing the electrical properties of the specimen during the operation of the drive means.

The invention may also be incorporated into a method for concurrently testing the mechanical and electrical properties of an electrically conductive specimen adapted for use in sealing gaps between aircraft panels, comprising providing a device having a pair of electrically conductive interior plates positionable on opposite sides of a specimen, a pair of electrically insulative intermediate plates located on the sides of the interior plates remote from the specimen, and a pair of electrically conductive exterior plates located on the sides of the intermediate plates remote from the specimen; coupling the exterior plates to drive means; operating the drive means to impart motion to the exterior plates with respect to the specimen; and attaching the interior plates to electrical means for providing electrical current and for testing the electrical properties of the speciment during the operation of the drive means.

The invention may also be incorporated into a method for concurrently testing the mechanical and electrical properties of an electrically conductive specimen adapted for use in sealing gaps between aircraft panels, comprising the steps of providing a device having a pair of electrically insulating primary plates with interior portions spaced from each other, and a pair of electrically conductive secondary plates secured to the interior portions of the primary plates so as to form a specimen-receiving space located entirely over only the interior portion of one of the primary plates; coupling a drive means with respect to the primary plates; operating the drive means to impart motion to at least one of the primary plates and its secured secondary plate with respect to the specimen; and attaching the secondary plates to electrical means for providing electrical current and for testing the electrical properties of the specimen during the operation of the drive means.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific embodiment may be readily utilized as a basis for modifying or designing other methods and structures for carrying out the same purposes of the present invention. It should also be realized by those skilled in the art that such equivalent methods and structures do not depart from the spirit and scope of the invention as set forth in the appended claims.

BRIEF DESCRIPTION OF THE DRAWINGS

For a fuller understanding of the nature and objects of the invention, reference should be had to the following detailed description taken in conjunction with the accompanying drawings in which:

FIG. 7 is an exploded perspective view of the second test device shown in FIG. 6.

Similar reference numbers refer to similar parts throughout the several Figures.

DETAILED DESCRIPTION OF THE INVENTION

Figure 1:
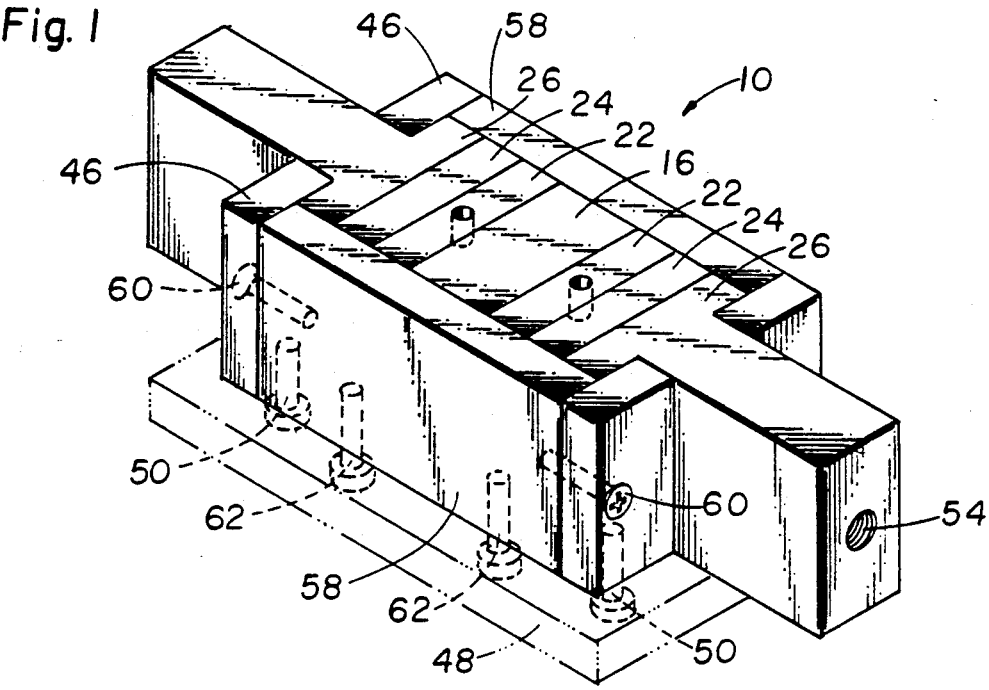
FIG. 1 is a perspective view of a first test device and associated support fixture constructed in accordance with the principles of the present invention.
Figure 2:
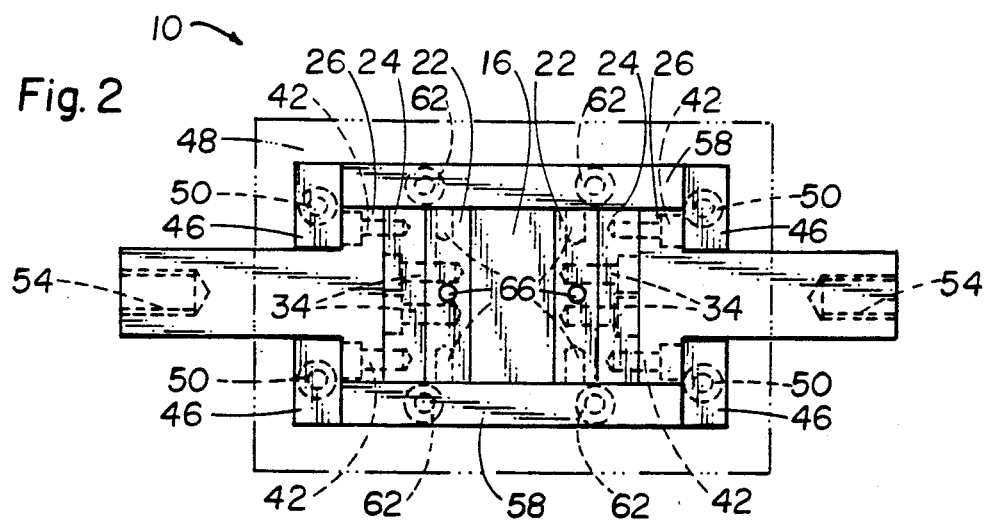
FIG. 2 is a plan view of the test device and support fixture illustrated in FIG. 1.
Figure 3:
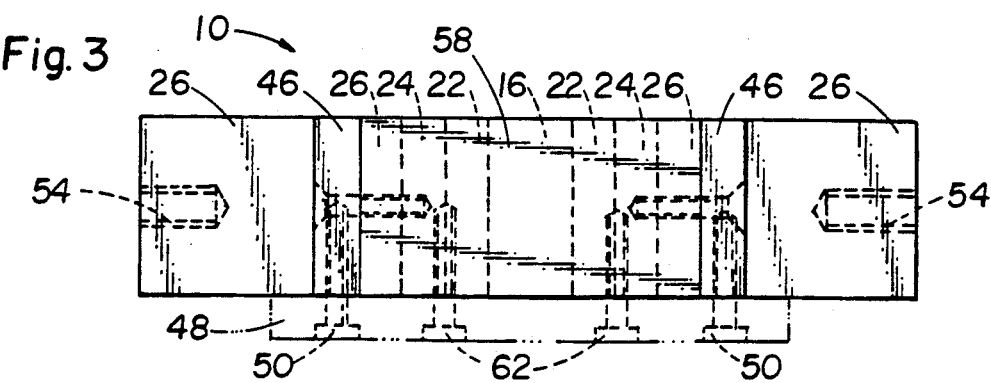
FIG. 3 is an elevational view of the test device and support fixture illustrated in FIGS. 1 and 2.
Figure 4:
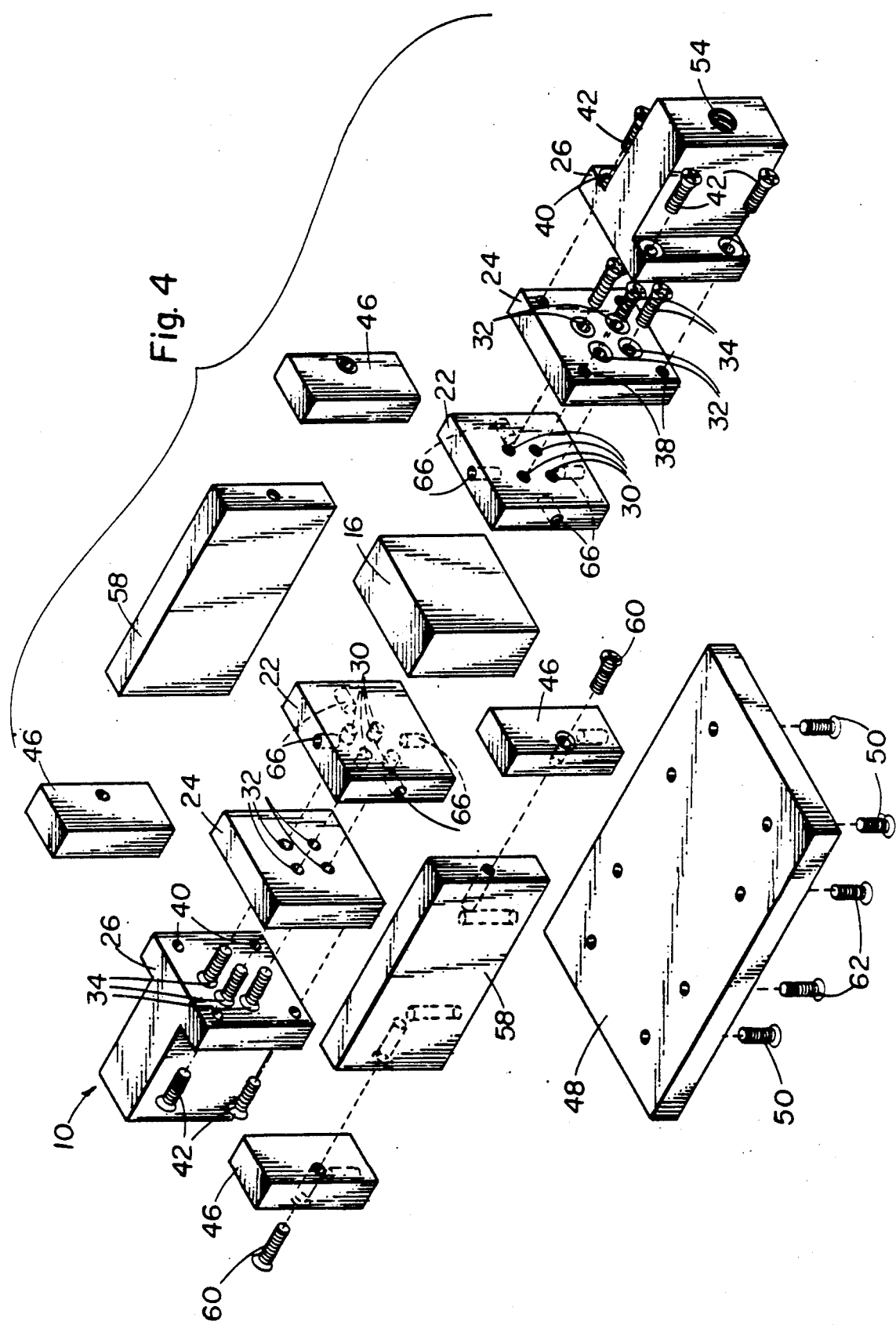
FIG. 4 is an exploded perspective view showing portions of the test device and support fixture illustrated in FIGS. 1 through 3.
Figure 5:
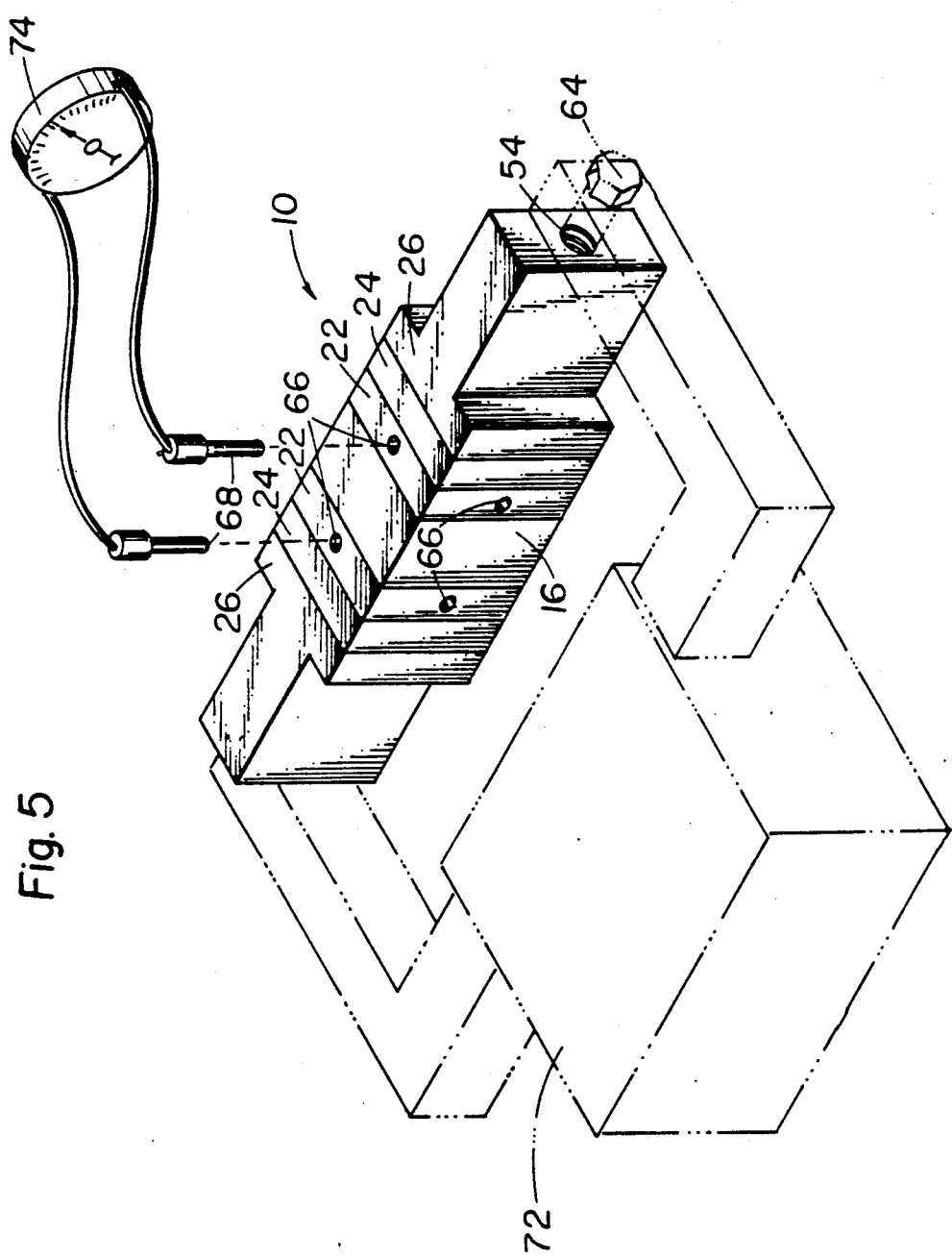
FIG. 5 is a perspective view of the test device shown in FIGS. 1 through 4, the test device being removed from the support fixture and coupled to test machinery.
Figure 6:
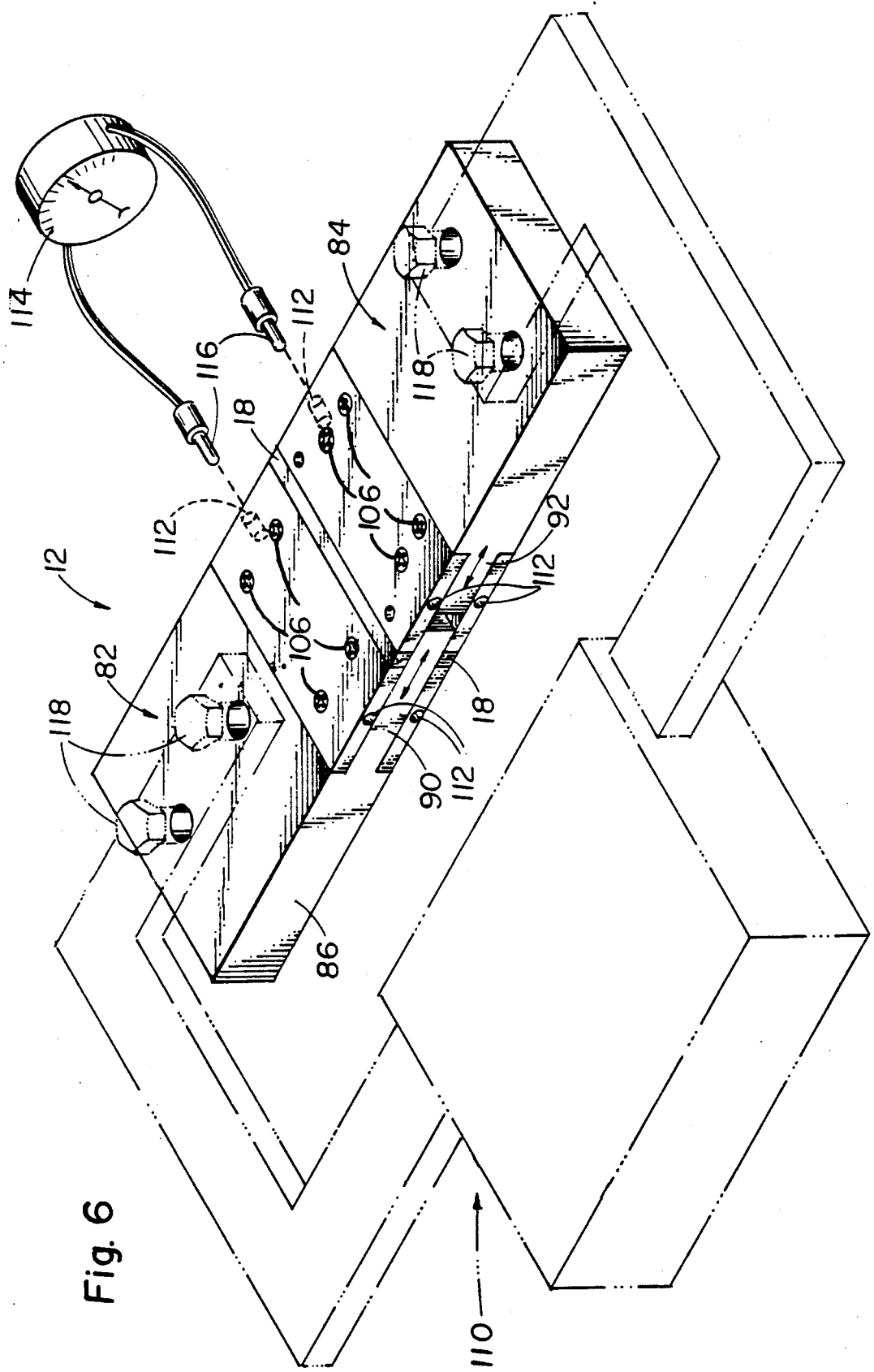
FIG. 6 is a perspective view of a second test device constructed in accordance with the principles of the present invention, the device being coupled to test machinery.

Shown in the drawings are a pair of devices 10 and 12 which when used in association with each other will test the mechanical and electrical properties of the material to be used as fillers for gaps between aircraft panels or plates. FIGS. 1 through 5 relate to fixture type 1 device 10. FIGS. 6 and 7 relates to test fixture 2 device 12. Test fixture 1 is a fixture for a test specimen 16 designed to test the tensile strength, elongation, adhesion and compression bulge of a specimen 16 which can be placed in environments and can be used at all temperatures. Test fixture 2 is a gap fatigue fixture for a specimen 18 and is comparable with present gap fatigue fixture for use with conductive gap tape except that the present device is designed for electrical testing during mechanical movement.

Test fixture 1 is a device 10 which comprises a pair of spaced, electrically conductive, interior plates 22. The plates are axially aligned and positionable on opposite sides of the specimen to be tested. They are rectangular in shape and are fabricated of an electrically conductive material such as aluminium, copper, silver or the like.

Located on the sides of the interior plates remote from the specimen are a pair of spaced, electrically insulative, intermediate plates 24. The intermediate plates are also rectangular and are axially aligned with the interior plates. They are fabricated of an electrically insulating material such as fiber reinforced polyelethene, FRP or the like.

Located on the sides of the intermediate plates remote from the specimen are a pair spaced, electrically conductive, exterior plates 26. These plates are also rectangular and are aligned with the interior and intermediate plates. The preferred materials for these exterior plates are an electrically conductive material such as aluminium, steel or the like.

The interior and intermediate plates are each formed with four corner holes 30 and 32 for the receipt of bolts 34 so as to retain the bolted plates together during relative movement with each other. The holes 32 of the interior plates are threaded for the receipt and support of their bolts. Similarly, the exterior and intermediate plates are also each formed with four corner holes 38 and 40, offset from the other corner holes, for the receipt of bolts 42 so as to retain the bolted plates together during relative movement with each other. The holes 40 of the intermediate plates are threaded for the receipt and support of their bolts.

The component elements of the device 10 are received and supported in proper position with respect to the specimen-receiving space by a test fixture. The test fixture includes pairs of corner blocks 46 which are secured to an end wall 48 through bolts 50 received in threaded holes of the blocks. In addition, spaced side walls 58 are secured to the end wall and corner blocks through bolts 60 and 62 received in threaded holes of the side walls. Together the end wall with the corner blocks and side walls form a fixture for receiving and supporting the test device in proper position during the forming of the specimen. The various components of the test fixture are preferably fabricated of a rigid metal such as aluminum. The surface of the side walls and end wall which are located to be contacted by the specimen are coated with a non-stick surface such as Teflon. In the alternative, these walls may be fabricated entirely of teflon.

One additional hole 54 is formed in outwardly extending projections of each of the exterior plates, in a central extent thereof. This hole is for coupling to a drive shaft 64. The drive shafts, upper and lower, are coupled with respect to the exterior plates for imparting relative motion to the exterior, intermediate and interior plates and with respect to the specimen. A motion imparting mechanism such as a conventional tensile machine 72 is attachable through its jaws to the drive shafts 64 for the application of motion thereto during the various testing procedures.

Apertures 66 are formed in the interior plates for the attachment to electrical probes 68 of an electrical device 74 for the providing of electrical current and for the testing of the electrical properties of the specimen during the movement of the drive shafts.

Mechanical tests to be performed by the first device include tensile-compression, elongation-bulge, adhesion to substrate, electrical tests include conductitiy, resistivity or the like, even after exposure to operational fluids such as fuel, oil, etc. Such tests are preferably carried out at room temperature but may be done at such temperatures as −45° F. to 200° F.

All of the shear tests refer to flatwise shear where the movement between the surfaces of the specimen and adjacent adhered support surface is perpendicular to their plane of coupling. This is compared to overlap shear wherein the separation forces are parallel with the plane coupling the surfaces.

The second device 12 is also for testing the mechanical and electrical properties of an electrically conductive specimen 18 adapted for use in sealing gaps between aircraft panels. This device comprises a pair of horizontally disposed primary plates 82 and 84 of electrically insulating material such as fiber reinforced polyethylene, FRP or the like. The primary plates are axially aligned and laterally disposed with respect to each other. They have exterior portions 86 and 88 of a thicker height and interior portions 90 and 92 of a thinner height. The interior portions are of different lengths and spaced from each other to allow for relative longitudinal sliding movement of the primary plates with respect to each other.

A pair of horizontally disposed secondary plates 96, 98, 100 and 102 are axially aligned and laterally disposed with respect to each other. The secondary plates are fabricated of an electrically conductive material such as aluminium, graphite reinforced epoxy, glass reinforced epoxy or the like. They are secured to the interior portions of the primary plates as through bolts 106. The secondary plates are also spaced from each other thereby forming a specimen-receiving space located entirely over only one of the interior portions of the primary plate. This construction allows for longitudinal sliding movement of the primary plates and their secured secondary plates with respect to each other.

Proper positioning and installation of each specific secondary plate with respect to its associated specific primary plate is effected by the use of alignment holes in the primary and secondary plates. More particularly, each seconday plate if formed with a unique number of alignment holes adjacent to an edge thereof which is positionable adjacent to a corresponding edge of its associated primary plate. When the number of holes of a secondary plate is positioned properly with respect to the same number of holes of its primary plate, such plates are properly aligned and may then be bolted together.

Driving mechanisms of a conventional fatigue test machine 110 are coupled through its jaws to the parallel surfaces of the thick portion of the primary plates for imparting motion to the primary and secondary plates with respect to the specimen. Such coupling and motion are required to effect the testing of the specimen.

Lastly, apertures 112 are formed in the secondary plates. The apertures function as attachment means to couple one of the planarly aligned pairs of secondary plates to electrical machinery 114 through probes 116. This is for providing electrical current and for the testing of the electrical properties of the specimen during the movement of the drive mechanisms.

Mechanical tests to be preformed by this second device include gap fatigue testing and the like. Electrical tests include conductivity/resistivity and the like.

In carrying out the method of the present invention, there is first provided a first device 10 as described above. The device is positioned within a support fixture, also as described above. The specimen 16 to be tested is then formed between the spaced interior plates 22 of the device. Thereafter, the device and specimen are removed from the support fixture and the exterior plates are coupled to the jaws of a tensile machine. The tensile machine is then operated to impart motion to the plates. The interior plates 22 are attached to electrical means for providing electrical current and for testing the electrical properties of the specimen during the operation of the tensile machine.

The method also includes the steps of providing a second device 12 as described above. The specimen 18 to be tested is then formed between spaced secondary plates of the device 12, first on one side then, if desired, on the other after the first side specimen has set up. Thereafter, the device and specimen are coupled to the jaws of a fatigue test machine through appropriate bolts 118. The fatigue test machine is operated to impart motion to the plates. The secondary plates 80 are attached to electrical means for providing electrical current and for testing the electrical properties of the specimen during the operation of the fatigue test machine.

The present disclosure includes that contained in the appended claims as well as that of the foregoing description. Although this invention has been described in its preferred forms with a certain degree of particularity, it is understood that the present disclosure of the preferred form has been made only by way of example and numerous changes in the details of contruction and combination and arrangement of parts may be resorted to without departing from the spirit and scope of the invention.

What is claimed is:

1. Apparatus for testing properties during movement of an electrically conductive specimen of a material adapted for use in sealing gaps between panels of aircraft, comprising:
   a pair of spaced, electrically conductive, interior plates aligned and positionable on opposite sides of the specimen to be tested;
   a pair of spaced, electrically insulative, intermediate plates aligned with the interior plates and located on first sides of the interior plates remote from the specimen;
   a pair of spaced, electrically conductive, exterior plates aligned with the interior and intermediate plates and located on second sides of the intermediate plates remote from the specimen;
   a support fixture having an end wall, corner blocks coupled to the end wall, and side walls coupled to the end wall and the corner blocks, the support fixture receiving and holding the exterior, intermediate and interior plates in proper position for receiving the specimen;
   bolts coupling the exterior, intermediate and interior plates on each side of the specimen together for insuring concurrent movement of the plates on each side of the specimen;
   shafts coupled to the exterior plates;
   drive means coupled to the shafts for imparting motion thereto;
   attachment means disposed in the interior plates for receiving electrical current and for testing of electrical properties of the specimen during operation of the drive means; and,
   electrical means connected to the attachment means for providing electrical current to the interior plates and for testing the electrical properties of the specimen during the operation of the drive means.

2. Apparatus for testing properties of an electrically conductive specimen of a material adapted for use in sealing gaps between aircraft panels, comprising:
   a pair of horizontally disposed primary plates of electrically insulating material axially aligned and laterally disposed with respect to each other, the primary plates having exterior portions of a thicker height and interior portions of a thinner height, the interior portions being of different lengths and spaced from each other to allow for relative longitudinal sliding movement of the primary plates with respect to each other;
   a pair of horizontally disposed secondary plates of electrically conductive material axially aligned and laterally disposed with respect to each other, the secondary plates being secured to the interior portions of the primary plates, the secondary plates being spaced from each other thereby forming a specimen-receiving space located entirely over only one of the interior portions of the primary plate for thereby allowing longitudinal sliding movement of the primary plates and their secured secondary plates with respect to each other;
   drive means coupled to the primary plates for imparting motion to the primary and secondary plates with respect to the specimen;
   attachment means disposed in the secondary plates for receiving electrical current and for testing of electrical properties of the specimen during the motion of the primary and secondary plates with respect to the specimen; and,
   electrical means connected to the attachment means for providing electrical current to the secondary plates and for testing the electrical properties of the specimen during the motion of the primary and secondary plates with respect to the specimen.

3. Apparatus for testing a specimen, comprising:
   a pair of spaced, electrically conductive, interior plates positionable on opposite sides of the specimen;
   a pair of spaced, electrically insulative, intermediate plates located on first sides of the interior plates remote from the specimen;
   a pair of spaced, electrically conductive, exterior plates located on second sides of the intermediate plates remote from the specimen;
   shafts coupled to the exterior plates;
   drive means coupled to the shafts for imparting motion thereto;
   coupling means disposed in the interior plates for receiving electrical current and for testing the specimen during operation of the drive means; and,
   electrical means connected to the coupling means for providing electrical current to the interior plates and for testing electrical properties of the specimen during operation of the drive means.

4. The apparatus as set forth in claim 3 wherein the plates all have a plurality of holes extending therethrough and further including bolts coupling the plates on opposite sides of the specimen together for concurrent movement with respect to the specimen.

5. The apparatus as set forth in claim 3 and further including a support fixture having an end wall, corner blocks secured to the end wall, and side walls secured to the corner blocks and the end wall, the support fixture receiving and holding the exterior, intermediate and interior plates in proper position for receiving the specimen.

6. Apparatus for testing a specimen comprising:
a pair of primary plates of electrically insulating material, the primary plates having exterior portions and interior portions, the interior portions being spaced from each other;
a pair of secondary plates of electrically conductive material, the secondary plates being secured to the interior portions of the primary plates, the secondary plates being spaced from each other thereby forming a specimen-receiving space therebetween located entirely over only the interior portion of one of the primary plates for thereby allowing relative longitudinal sliding movement of the primary plates and their secured secondary plates with respect to each other and the specimen;
drive means coupled to the primary plates for imparting motion to at least one of the primary plates and its secured secondary plates with respect to the specimen;
attachment means disposed in the secondary plates for receiving electrical current and for testing electrical properties of the specimen during operation of the drive means; and,
electrical means connected to the attachment means for providing electrical current to the secondary plates and for testing the electrical properties of the speciment during operation of the drive means.

7. The apparatus as set forth in claim 6 and further including a second pair of supplemental plates located on the interior portions of the primary plates opposite from the first pair of secondary plates.

8. A method for concurrently testing the mechanical and electrical properties of an electrically conductive specimen of a material adapted for use in sealing gaps between aircraft panels, comprising the steps of:
positioning a pair of electrically conductive interior plates, a pair of electrically insulative intermediate plates, and a pair of electrically conductive exterior plates within a support fixture, the support fixture having an end wall, corner blocks secured to the end wall, and side walls secured to the end wall and to the corner blocks, the interior plates being positioned on opposite sides of a specimen-receiving region, the intermediate plates being positioned on first sides of the interior plates remote from the specimen-receiving region, the exterior plates being positioned on second sides of the intemediate plates remote from the specimen-receiving region;
securing the interior, intermediate, and exterior plates on each side of the specimen-receiving region together for concurrent movement with each other relative to the specimen;
disposing the specimen in the specimen-receiving region;
removing the specimen and the interior, intermediate, and exterior plates from the support fixture;
coupling the exterior plates to drive means;
operating the drive means to impart motion to the exterior plates with respect to the specimen;
attaching the interior plates to electrical means for providing electrical current and for testing the electrical properties of the specimen during the operation of the drive means; and,
operating the electrical means to provide the electrical current to the interior plates and to test the electrical properties of the specimen during the operation of the drive means.

9. A method for concurrently testing mechanical and electrical properties of an electrically conductive specimen of a material adapted for use in sealing gaps between aircraft panels, comprising the steps of:
forming the specimen in a device having a pair of electrically insulating primary plates with interior portions spaced from each other and a pair of electrically conductive secondary plates secured to the interior portions of the primary plates, the specimen being formed in a specimen-receiving space located entirely over only the interior portion of one of the primary plates;
coupling the primary plates to a drive means;
operating the drive means to impart motion to at least one of the primary plates and its secured secondary plate with respect to the specimen;
attaching the secondary plates to electrical means for providing electrical current and for testing the electrical properties of the specimen during the operation of the drive means; and,
operating the electrical means to provide the electrical current to the secondary plates and to test the electrical properties of the specimen during the operation of the drive means.

* * * * *